(12) United States Patent
Kuczaj

(10) Patent No.: US 10,512,285 B2
(45) Date of Patent: Dec. 24, 2019

(54) METHOD OF CONTROLLING AEROSOL PRODUCTION TO CONTROL AEROSOL PROPERTIES

(71) Applicant: Philip Morris Products S.A., Neuchatel (CH)

(72) Inventor: Arkadiusz Kuczaj, Colombier (CH)

(73) Assignee: Philip Morris Products S.A., Neuchatel (CH)

( * ) Notice: Subject to any disclaimer, the term of this patent is extended or adjusted under 35 U.S.C. 154(b) by 0 days.

(21) Appl. No.: 15/535,473

(22) PCT Filed: Dec. 4, 2015

(86) PCT No.: PCT/EP2015/078690
§ 371 (c)(1),
(2) Date: Jun. 13, 2017

(87) PCT Pub. No.: WO2016/096482
PCT Pub. Date: Jun. 23, 2016

(65) Prior Publication Data
US 2017/0360094 A1    Dec. 21, 2017

(30) Foreign Application Priority Data
Dec. 15, 2014    (EP) .................................... 14198062

(51) Int. Cl.
*A24F 47/00*    (2006.01)
*A61M 11/04*    (2006.01)
(Continued)

(52) U.S. Cl.
CPC ......... *A24F 47/008* (2013.01); *A61M 11/042* (2014.02); *A61M 15/06* (2013.01);
(Continued)

(58) Field of Classification Search
CPC ..................................................... A24F 47/008
See application file for complete search history.

(56) References Cited

U.S. PATENT DOCUMENTS

2009/0230117 A1    9/2009  Fernando et al.
2011/0155153 A1    6/2011  Thorens et al.
(Continued)

FOREIGN PATENT DOCUMENTS

EP            2 399 636 A1    12/2011
WO    WO 2009/132793 A1    11/2009
(Continued)

OTHER PUBLICATIONS

International Search Report and Written Opinion dated May 31, 2016 in PCT/EP2015/078690, filed Dec. 4, 2015.

*Primary Examiner* — Eric Yaary
(74) *Attorney, Agent, or Firm* — Oblon, McClelland, Maier & Neustadt, L.L.P.

(57) ABSTRACT

There is provided a method of controlling aerosol production in an aerosol-generating device including a heater including at least one heating element, an aerosol-forming substrate disposed and configured to be heated by the heating element, and a power source configured to provide power to the heating element; the method including providing a period of gas flow over the substrate, the gas flow rate varying during the period, providing power to the heating element such that the substrate is heated and volatile components of the substrate are entrained in the gas flow, thereby forming an entrained gas flow, and allowing the entrained gas flow to cool such that the volatile components condense and form an aerosol, wherein the power provided to the heating element during the period is controlled such that one or more physical and/or chemical characteristics of the aerosol are maintained at a substantially constant value during the period.

7 Claims, 3 Drawing Sheets

(51) Int. Cl.
*A61M 15/06* (2006.01)
*A61M 16/00* (2006.01)

(52) U.S. Cl.
CPC ............... *A61M 2016/0024* (2013.01); *A61M 2205/3334* (2013.01); *A61M 2205/3368* (2013.01)

(56) References Cited

U.S. PATENT DOCUMENTS

| | | |
|---|---|---|
| 2012/0291791 A1 | 11/2012 | Pradeep |
| 2013/0104916 A1 | 5/2013 | Bellinger et al. |
| 2013/0284192 A1* | 10/2013 | Peleg .................... A24F 47/002 131/329 |
| 2014/0299141 A1 | 10/2014 | Flick |
| 2014/0332016 A1 | 11/2014 | Bellinger et al. |
| 2014/0334802 A1* | 11/2014 | Dubief ...................... A61L 9/03 392/390 |
| 2014/0353856 A1* | 12/2014 | Dubief .................. A24D 3/041 261/128 |
| 2016/0044963 A1 | 2/2016 | Saleem |
| 2017/0079110 A1* | 3/2017 | Plattner ................ A61M 15/06 |

FOREIGN PATENT DOCUMENTS

| | | | |
|---|---|---|---|
| WO | WO 2013/060781 A1 | 5/2013 | |
| WO | WO 2013/060784 A2 | 5/2013 | |
| WO | WO 2013/083635 A1 | 6/2013 | |
| WO | WO-2013083636 A1 * | 6/2013 | ............. A24D 3/041 |
| WO | WO-2013083638 A1 * | 6/2013 | ........... A24F 47/008 |
| WO | WO 2014/147114 A1 | 9/2014 | |

\* cited by examiner

METHOD OF CONTROLLING AEROSOL PRODUCTION TO CONTROL AEROSOL PROPERTIES

The present invention relates to methods for controlling aerosol production. The present invention further relates to an aerosol-generating device and more specifically to an electrically-operated aerosol-generating device, for example a smoking device. The present invention finds particular application as a method for controlling aerosol production in an aerosol-generating device to deliver a consistent aerosol.

WO-A-2009/132793 discloses an example of an electrically heated smoking device and system. In this device a liquid is stored in a liquid storage portion, and a capillary wick has a first end which extends into the liquid storage portion for contact with the liquid therein, and a second end which extends out of the liquid storage portion. A heating element heats the second end of the capillary wick. The heating element is in the form of a spirally wound electric heating element in electrical connection with a power supply, and surrounding the second end of the capillary wick. In use, the heating element may be activated by the user to switch on the power supply. Suction on a mouthpiece by the user causes air to be drawn into the electrically heated smoking system over the capillary wick and heating element and subsequently into the mouth of the user.

In general, an electrically-operated aerosol generating device comprises of at least one heating element, which is usually thermally controlled by reference to delivered power. As an alternative, the heating element or elements may be thermally controlled by reference to the temperature of the heating element. Heating may start per user request or may be activated by a suitable puff-detection system. Both power and temperature controlled devices suffer from a lack of control on the properties and characteristics of a delivered aerosol due to uncontrolled heating process during the puff duration.

When a user puffs on an aerosol-generating device air flows through the device. A power controlled device will deliver a constant power to the heating element. With an increasing ambient flow rate through the device, the temperature of the heating element will decrease. This will result in change in the chemical and/or physical characterization of the formed aerosol droplets. For example, a decreasing temperature of the heating element may lead to formation of different aerosol constituents. Decreasing temperature and increasing flow rate tend to cause a decrease in cooling rate, which will alter the aerosol droplet size.

In a temperature controlled system air flow over the heating element will result in increased power being supplied to the heating element due to local cooling of the heating filaments. This increase of power compensates for the convection-diffusion dictated local loss of energy due to cooling with the air flow. Changes in the flow rate may result in variations in the mixing efficiency of the air and aerosol components generated by the heater as well as causing variations in cooling rate, which affect aerosol droplet size. The increased power consumption based on flow rate will also reduce battery life-time.

A method of controlling aerosol production in an aerosol-generating device is provided. The aerosol-generating device comprises a heater comprising at least one heating element, an aerosol-forming substrate located such that it can be heated by the heating element, and a power source for providing power to the heating element. The method comprises the steps of providing a period of gas flow over the aerosol-forming substrate, the gas flow rate varying during the period of gas flow, providing power to the heating element such that the aerosol-forming substrate is heated and volatile components of the aerosol-forming substrate are entrained in the gas flow, thereby forming an entrained gas flow, and allowing the entrained gas flow to cool such that the volatile components condense and form an aerosol. The power provided to the heating element during the period of gas flow is controlled such that one or more physical and/or chemical characteristics of the aerosol are maintained at a substantially constant value during the period of gas flow. Substantially constant may mean that the characteristic varies by no more than 10% during the period of gas flow. Preferably the characteristic varies by no more than 5% during the period of gas flow.

The power provided to the heating element during the period of gas flow may be controlled such that mixing efficiency of the entrained gas flow and/or cooling rate of the entrained gas flow are maintained at a substantially steady state during the period of gas flow.

Heated gas with entrained volatile components mixes with cooler gas during the period of gas flow. The combined streams of gas cool to allow aerosol to form. Mixing or mixing efficiency is a parameter that can be used to give an indication of the ability of a device, under certain conditions, to produce a homogenous mixture. Mixing efficiency can depend on many factors, including device geometry, gas flow rate, and relative temperature of the gases. Mixing efficiency may be represented by a normalised parameter. For example, mixing efficiency may be represented by $\eta=4\theta(1-\theta)$, where $\theta=((T-T_{min})/(T_{max}-T_{min}))$. This parameter is based on the assumption that the ultimate mixing state of the same amount of gases with two different temperatures will result in $\theta=1/2$ and consequently, $\eta=1$. For a given device geometry the mixing efficiency may vary considerably as a function of gas flow rate and heating element temperature. Control of the mixing efficiency may In order to form a consistent aerosol over the duration of the gas flow period it is preferred that the mixing efficiency, as represented by any suitable parameter, is substantially constant over the duration of the gas flow period. Thus, it may be preferred that the power supplied to the heating element is controlled during the gas flow period so as to maintain the mixing efficiency at substantially constant levels.

The cooling rate of the gas containing the entrained volatile components has a significant influence on aerosol parameters and in particular on aerosol droplet size. In order to obtain an aerosol that has consistent aerosol droplet size it may be preferred that the power supplied to the heating element is controlled during the gas flow period so as to maintain the cooling rate at substantially constant levels.

It may be preferred to design a heating profile for any given device that maximizes and creates quasi-steady cooling rate and mixing efficiency. Such a heating profile or thermal profile may be created for any specific device and then implemented in real time by adapting the heating profile based on feedback from a volume flow sensor in the device.

Preferably, one or more physical characteristics of the aerosol selected from the list consisting of concentration of volatile component, droplet number density, and droplet size, are maintained at a substantially constant value during the period of gas flow.

It may be preferred to monitor parameters in real time and control a heating profile that maximizes and creates quasi-steady cooling rate and mixing efficiency. Values representative of one or more parameter selected from the list consisting of gas flow rate, gas flow temperature, vaporisation rate, and heating element temperature may be measured or calculated in real time and used to control the power provided to the heating element during the period of gas flow.

The heating profile, either pre-determined or generated in real time, may involve the power provided to the heating element being reduced to zero for one or more period of time during the period of gas flow.

A method of controlling aerosol production in an aerosol-generating device may involve steps of providing power to the heating element such that the aerosol-forming substrate is heated and volatile components of the aerosol-forming substrate are entrained in the gas flow, thereby forming an entrained gas flow, and allowing the entrained gas flow to cool such that the volatile components condense and form an aerosol, in which the power provided to the heating element is controlled with reference to the gas flow rate so as to control the physical and/or chemical properties of the aerosol. The power to the heating element may be switched off before the end of the period of gas flow.

The aerosol-generating device may be an electrically-operated aerosol-generating device, for example a smoking device, and the period of gas flow may be provided by a user puffing on the device.

The heater may comprise a single heating element. Alternatively, the heater may comprise more than one heating element, for example two, or three, or four, or five, or six or more heating elements. The heating element or heating elements may be arranged appropriately so as to most effectively heat the aerosol-forming substrate.

The at least one heating element preferably comprises an electrically resistive material. Suitable electrically resistive materials include but are not limited to: semiconductors such as doped ceramics, electrically "conductive" ceramics (such as, for example, molybdenum disilicide), carbon, graphite, metals, metal alloys and composite materials made of a ceramic material and a metallic material. Such composite materials may comprise doped or undoped ceramics.

Examples of suitable doped ceramics include doped silicon carbides. Examples of suitable metals include titanium, zirconium, tantalum and metals from the platinum group. Examples of suitable metal alloys include stainless steel, Constantan, nickel-, cobalt-, chromium-, aluminium- titanium- zirconium-, hafnium-, niobium-, molybdenum-, tantalum-, tungsten-, tin-, gallium-, manganese- and iron-containing alloys, and super-alloys based on nickel, iron, cobalt, stainless steel, Timetal®, iron-aluminium based alloys and iron-manganese-aluminium based alloys. Timetal® is a registered trade mark of Titanium Metals Corporation, 1999 Broadway Suite 4300, Denver Colo. In composite materials, the electrically resistive material may optionally be embedded in, encapsulated or coated with an insulating material or vice-versa, depending on the kinetics of energy transfer and the external physicochemical properties required. The heating element may comprise a metallic etched foil insulated between two layers of an inert material. In that case, the inert material may comprise Kapton®, all-polyimide or mica foil. Kapton® is a registered trade mark of E.I. du Pont de Nemours and Company, 1007 Market Street, Wilmington, Del. 19898, United States of America.

Alternatively, the at least one heating element may comprise an infra-red heating element, a photonic source, or an inductive heating element.

The at least one heating element may be an electric heating element and may take any suitable form. For example, the at least one electric heating element may take the form of a heating blade. Alternatively, the at least one electric heating element may take the form of a casing or substrate having different electro-conductive portions, or an electrically resistive metallic tube. If the aerosol-forming substrate is a liquid provided within a container, the container may incorporate a disposable heating element. Alternatively, one or more heating needles or rods that run through the centre of the aerosol-forming substrate may also be suitable. Alternatively, the at least one heating element may be a disk (end) heater or a combination of a disk heater with heating needles or rods. Alternatively, the at least one electric heating element may comprise a flexible sheet of material arranged to surround or partially surround the aerosol-forming substrate. Other alternatives include a heating wire or filament, for example a Ni—Cr, platinum, tungsten or alloy wire, or a heating plate. Optionally, the heating element may be deposited in or on a rigid carrier material.

The at least one heating element may comprise a heat sink, or heat reservoir comprising a material capable of absorbing and storing heat and subsequently releasing the heat over time to the aerosol-forming substrate. The heat sink may be formed of any suitable material, such as a suitable metal or ceramic material. Preferably, the material has a high heat capacity (sensible heat storage material), or is a material capable of absorbing and subsequently releasing heat via a reversible process, such as a high temperature phase change. Suitable sensible heat storage materials include silica gel, alumina, carbon, glass mat, glass fibre, minerals, a metal or alloy such as aluminium, silver or lead, and a cellulose material such as paper. Other suitable materials which release heat via a reversible phase change include paraffin, sodium acetate, naphthalene, wax, polyethylene oxide, a metal, metal salt, a mixture of eutectic salts or an alloy.

The heat sink or heat reservoir may be arranged such that it is directly in contact with the aerosol-forming substrate and can transfer the stored heat directly to the substrate. Alternatively, the heat stored in the heat sink or heat reservoir may be transferred to the aerosol-forming substrate by means of a heat conductor, such as a metallic tube.

The at least one heating element may heat the aerosol-forming substrate by means of conduction. The heating element may be at least partially in contact with the substrate, or the carrier on which the substrate is deposited. Alternatively, the heat from the heating element may be conducted to heat conductive element.

Alternatively, the at least one heating element may transfer heat to the incoming ambient air that is drawn through the electrically heated aerosol generating device during use, which in turn heats the aerosol-forming substrate by convection. The ambient air may be heated before passing through the aerosol-forming substrate. Alternatively, if the aerosol-forming substrate is a liquid substrate, the ambient air may be first drawn through the substrate and then heated.

The aerosol-forming substrate may be a solid aerosol-forming substrate. The aerosol-forming substrate preferably comprises a tobacco-containing material containing volatile tobacco flavour compounds which are released from the substrate upon heating. The aerosol-forming substrate may comprise a non-tobacco material. The aerosol-forming substrate may comprise tobacco-containing material and non-tobacco containing material. Preferably, the aerosol-forming substrate further comprises an aerosol former. Examples of suitable aerosol formers are glycerine and propylene glycol.

Alternatively, the aerosol-forming substrate may be a liquid aerosol-forming substrate. In one embodiment, the aerosol-generating device further comprises a liquid storage portion. Preferably, the liquid aerosol-forming substrate is stored in the liquid storage portion. In one embodiment, the electrically heated aerosol generating device further comprises a capillary wick in communication with the liquid storage portion. It is also possible for a capillary wick for holding liquid to be provided without a liquid storage portion. In that embodiment, the capillary wick may be preloaded with liquid.

Preferably, the capillary wick is arranged to be in contact with liquid in the liquid storage portion. In that case, in use, liquid is transferred from the liquid storage portion towards the at least one electric heating element by capillary action in the capillary wick. In one embodiment, the capillary wick has a first end and a second end, the first end extending into the liquid storage portion for contact with liquid therein and the at least one electric heating element being arranged to heat liquid in the second end. When the heating element is activated, the liquid at the second end of the capillary wick is vaporized by the heater to form the supersaturated vapour. The supersaturated vapour is mixed with and carried in the airflow. During the gas flow (airflow), the vapour condenses to form the aerosol and the aerosol is carried towards the mouth of a user. The heating element in combination with a capillary wick may provide a fast response, because that arrangement may provide a high surface area of liquid to the heating element. Control of the heating element according to the invention may therefore depend on the structure of the capillary wick arrangement.

The liquid substrate may be absorbed into a porous carrier material, which may be made from any suitable absorbent plug or body, for example, a foamed metal or plastics material, polypropylene, terylene, nylon fibres or ceramic. The liquid substrate may be retained in the porous carrier material prior to use of the electrically heated aerosol generating device or alternatively, the liquid substrate material may be released into the porous carrier material during, or immediately prior to use. For example, the liquid substrate may be provided in a capsule. The shell of the capsule preferably melts upon heating and releases the liquid substrate into the porous carrier material. The capsule may optionally contain a solid in combination with the liquid.

If the aerosol-forming substrate is a liquid substrate, the liquid has specific physical properties. These include, for example, a boiling point, vapour pressure, and surface tension characteristics to make them suitable for use in the aerosol generating device. Control of the at least one electric heating element may depend upon the physical properties of the liquid substrate. The liquid preferably comprises a tobacco-containing material comprising volatile tobacco flavour compounds which are released from the liquid upon heating.

Alternatively, or in addition, the liquid may comprise a non-tobacco material. The liquid may include water, solvents, ethanol, plant extracts and natural or artificial flavours. Preferably, the liquid further comprises an aerosol former. Examples of suitable aerosol formers are glycerine and propylene glycol.

An advantage of providing a liquid storage portion is that a high level of hygiene can be maintained. Using a capillary wick extending between the liquid and the electric heating element, allows the structure of the device to be relatively simple. The liquid has physical properties, including viscosity and surface tension, which allow the liquid to be transported through the capillary wick by capillary action. The liquid storage portion is preferably a container. The liquid storage portion may not be refillable. Thus, when the liquid in the liquid storage portion has been used up, the liquid storage portion, or the entire aerosol generating device, is replaced. Alternatively, the liquid storage portion may be refillable. In that case, the aerosol generating device may be replaced after a certain number of refills of the liquid storage portion. Preferably, the liquid storage portion is arranged to hold liquid for a pre-determined number of puffs.

The capillary wick may have a fibrous or spongy structure. The capillary wick preferably comprises a bundle of capillaries. For example, the capillary wick may comprise a plurality of fibres or threads, or other fine bore tubes. The fibres or threads may be generally aligned in the longitudinal direction of the aerosol generating device. Alternatively, the capillary wick may comprise sponge-like or foam-like material formed into a rod shape. The rod shape may extend along the longitudinal direction of the aerosol generating device. The structure of the wick forms a plurality of small bores or tubes, through which the liquid can be transported to the electric heating element, by capillary action. The capillary wick may comprise any suitable material or combination of materials. Examples of suitable materials are ceramic- or graphite-based materials in the form of fibres or sintered powders. The capillary wick may have any suitable capillarity and porosity so as to be used with different liquid physical properties such as density, viscosity, surface tension and vapour pressure. The capillary properties of the wick, combined with the properties of the liquid, ensure that the wick is always wet in the heating area.

The aerosol-forming substrate may alternatively be any other sort of substrate, for example, a gas substrate, or any combination of the various types of substrate. During operation, the substrate may be completely contained within the electrically heated aerosol generating device. In that case, a user may puff on a mouthpiece of the electrically heated aerosol generating device. Alternatively, during operation, the substrate may be partially contained within the electrically heated aerosol generating device. In that case, the substrate may form part of a separate article and the user may puff directly on the separate article.

Preferably, the electrically heated aerosol generating device is an electrically heated smoking device. The electrically heated aerosol generating device may comprise an aerosol-forming chamber in which aerosol forms from a super saturated vapour, which aerosol is then carried into the mouth of the user. An air inlet, air outlet and the chamber are preferably arranged so as to define an airflow route from the air inlet to the air outlet via the aerosol-forming chamber, so as to convey the aerosol to the air outlet and into the mouth of a user.

Preferably, the aerosol generating device comprises a housing. Preferably, the housing is elongate. The structure and geometry of the housing will influence the aerosol. The housing may comprise a shell and a mouthpiece. In that case, all the components may be contained in either the shell or the mouthpiece. The housing may comprise any suitable material or combination of materials. Examples of suitable materials include metals, alloys, plastics or composite materials containing one or more of those materials, or thermoplastics that are suitable for food or pharmaceutical applications, for example polypropylene, polyetheretherketone (PEEK) and polyethylene. Preferably, the material is light and non-brittle.

An electrically-operated aerosol-generating device may be provided. The device may comprise a heater comprising at least one heating element, an aerosol-forming substrate located such that it can be heated by the heating element and a power source for providing power to the heating element. The aerosol-generating device may comprise one or more sensors for sensing one or more parameters to enable real-time characterisation of an aerosol generated by the aerosol-generating device and a controller for controlling the power provided to the heating element based on the real time characterisation of the aerosol.

Preferably, the aerosol generating device is portable. The aerosol generating device may be a smoking device and may have a size comparable to a conventional cigar or cigarette. The smoking device may have a total length between approximately 30 mm and approximately 150 mm. The smoking device may have an external diameter between approximately 5 mm and approximately 30 mm.

Features described in relation to one aspect of the invention may be applicable to another aspect of the invention.

The invention will be further described, by way of example only, with reference to the accompanying drawings, in which.

Figure 1:
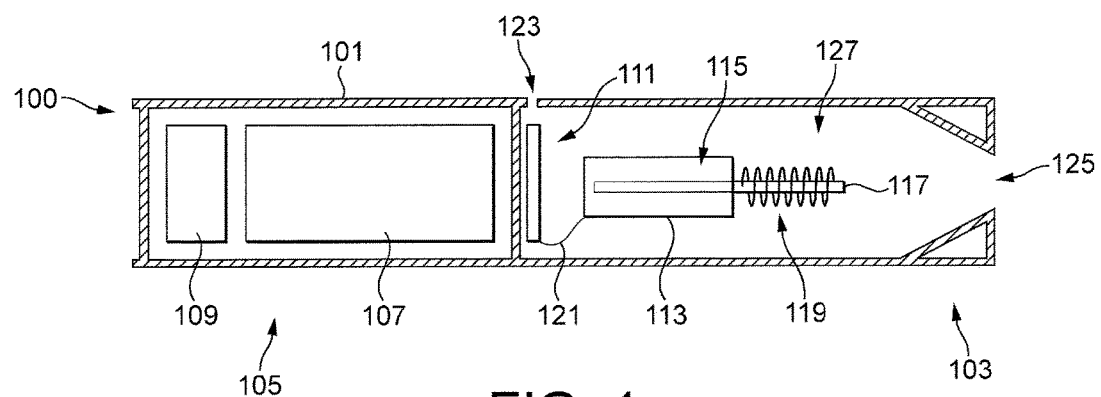
FIG. 1 shows one example of an electrically operated aerosol-generating device.

FIG. 1 shows one example of an electrically heated aerosol generating device. In FIG. 1, the device is a smoking device having a liquid storage portion. The smoking device 100 of FIG. 1 comprises a housing 101 having a mouthpiece end 103 and a body end 105. In the body end, there is provided an electric power supply in the form of battery 107 and electric circuitry in the form of hardware 109 and a puff detection device 111. In the mouthpiece end, there is provided a liquid storage portion in the form of cartridge 113 containing liquid 115, a capillary wick 117 and a heater 119 comprising at least one heating element. Note that the heater is only shown schematically in FIG. 1. One end of the capillary wick 117 extends into the cartridge 113 and the other end of the capillary wick 117 is surrounded by the heater 119. The heater is connected to the electric circuitry via connections 121. The housing 101 also includes an air inlet 123, an air outlet 125 at the mouthpiece end and an aerosol-forming chamber 127.

In use, operation is as follows. Liquid 115 is transferred or conveyed by capillary action from the cartridge 113 from the end of the wick 117 which extends into the cartridge to the other end of the wick 117 which is surrounded by the heater 119. When a user draws on the device at the air outlet 125, ambient air is drawn through air inlet 123. In the arrangement shown in FIG. 1, the puff detection device 111 senses the puff and activates the heater 119. The battery 107 supplies energy to the heater 119 to heat the end of the wick 117 surrounded by the heater. The liquid in that end of the wick 117 is vaporized by the heater 119 to create a super-saturated vapour. At the same time, the liquid being vaporized is replaced by further liquid moving along the wick 117 by capillary action. (This is sometimes referred to as "pumping action".) The supersaturated vapour created is mixed with and carried in the airflow from the air inlet 123. In the aerosol-forming chamber 127, the vapour condenses to form an inhalable aerosol, which is carried towards the outlet 125 and into the mouth of the user.

The capillary wick can be made from a variety of porous or capillary materials and preferably has a known, pre-defined capillarity. Examples include ceramic- or graphite-based materials in the form of fibres or sintered powders. Wicks of different porosities can be used to accommodate different liquid physical properties such as density, viscosity, surface tension and vapour pressure. The wick must be suitable so that the required amount of liquid can be delivered to the heating element. The wick and heating element must be suitable so that the required amount of aerosol can be conveyed to the user.

In the embodiment shown in FIG. 1, the flow rate during a puff and the temperature of the heater are monitored during a puff. Values representative of cooling rate and mixing efficiency are generated and a controller controls power to the heater. This allows a heating profile for the duration of the puff to be managed such that cooling rate and mixing efficiency are maintained at approximately constant levels.

FIG. 1 shows one example of an electrically heated aerosol generating device which may be used with the present invention. Many other examples are usable with the invention, however. The electrically heated aerosol generating device simply needs to include or receive an aerosol forming substrate which can be heated by at least one electric heating element, powered by a power supply under the control of electric circuitry. For example, the device need not be a smoking device. For example, the aerosol forming substrate may be a solid substrate, rather than a liquid substrate. Alternatively, the aerosol forming substrate may be another form of substrate such as a gas substrate. The heating element may take any appropriate form. The overall shape and size of the housing could be altered and the housing could comprise a separable shell and mouthpiece. Other variations are, of course, possible.

Figure 2:
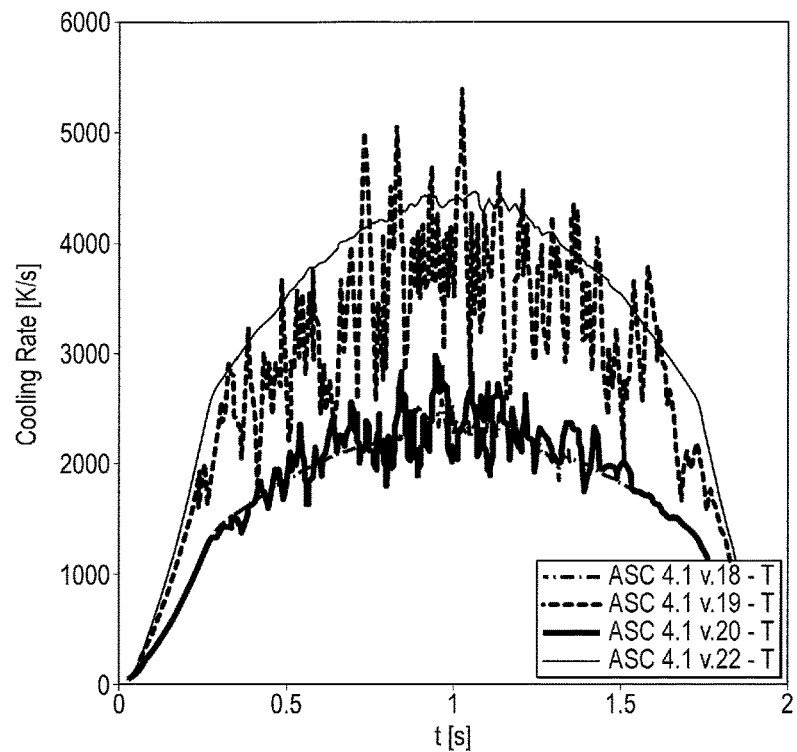
FIG. 2 is a graph illustrating a variation in cooling rate during a puff for a number of aerosol-generating devices.
Figure 3:
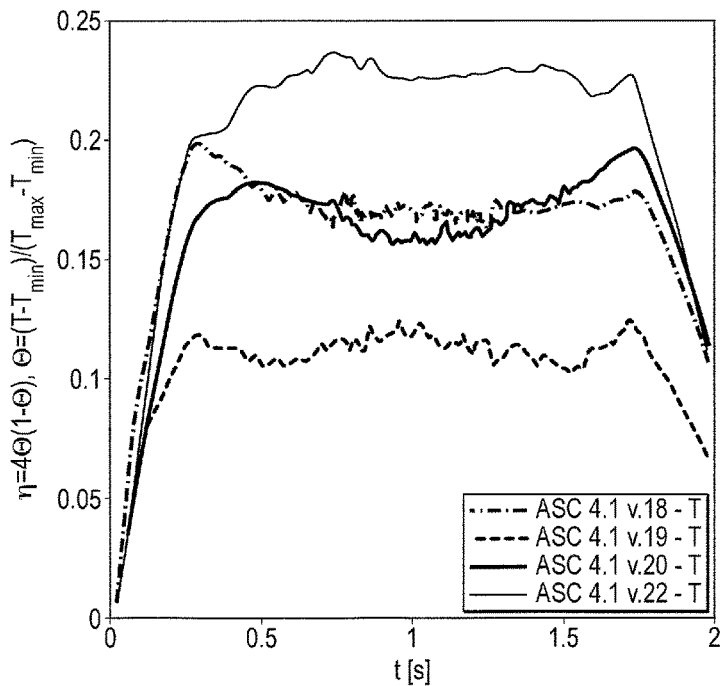
FIG. 3 is a graph illustrating a variation in mixing efficiency during a puff for a number of aerosol-generating devices.

FIG. 2 is a graph illustrating variations in cooling rate of air drawn through an aerosol-generating device over the duration of a puff. FIG. 3 is a graph illustrating variations in mixing efficiency of air drawn through an aerosol-generating device over the duration of a puff. Results in both FIG. 2 and FIG. 3 are representative of four different aerosol-generating devices having different geometries. All aerosol-generating devices were controlled such that the heating element was maintained at constant temperature. It can be clearly seen that, despite the constant temperature of the heating element, the cooling rate and mixing efficiency vary greatly over the puff profile. Thus, the properties of the aerosol generated vary over the puff profile.

Figure 4:
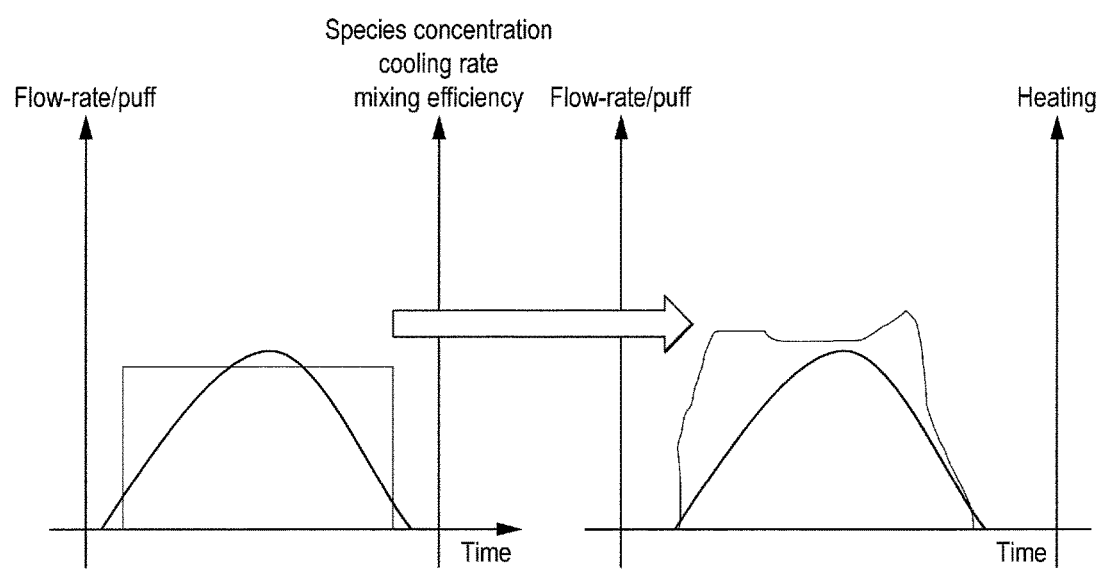
FIG. 4 provides schematic diagrams illustrating desirable aerosol properties over a puff duration and an example heating profile to achieve those properties.

FIG. 4 illustrates a desired situation in which characteristics such as species concentration, cooling rate, and mixing efficiency are maintained at a quasi-steady state during the puff duration, despite significant variation in puff profile. An example thermal profile is illustrated aimed at achieving the desired result. The desired result may be achieved by designing a specific thermal profile for a particular device structure and geometry, and then implementing the thermal profile based on measurement of flow rate through the device. Alternatively, the desired result may be achieved by monitoring parameters representative of mixing efficiency and/or cooling rate and controlling the power supplied to the heater based on those parameters. By use of one of these methods it is possible to produce a uniform aerosol over the duration of a puff.

The invention claimed is:

1. A method of controlling aerosol production in an aerosol-generating device,
   the device comprising:
   a heater comprising at least one heating element,
   an aerosol-forming substrate disposed and configured to be heated by the heating element, and a power source configured to provide power to the heating element; and the method comprising:
- providing a period of gas flow over the aerosol-forming substrate, the gas flow rate varying during the period of the gas flow,
- providing power to the heating element such that the aerosol-forming substrate is heated and volatile components of the aerosol-forming substrate are entrained in the gas flow, thereby forming an entrained gas flow, and
- allowing the entrained gas flow to cool such that the volatile components condense and form an aerosol,
- wherein the power provided to the heating, element dining the period of the gas flow is controlled such that a mixing efficiency of the volatile components in the entrained gas flow and a cooling rate of the volatile components in the entrained gas flow are maintained at a substantially steady state during the period of the gas flow.

2. The method according to claim 1,
wherein one or more physical characteristics of the aerosol include at least one characteristic of a concentration of a volatile component, a droplet number density, and a droplet size, and
wherein the one or more physical characteristics of the aerosol are maintained at a constant value during the period of the gas flow.

3. The method according to claim 2, wherein values representative of the one or more physical characteristics of the aerosol are measured or calculated in real time and are used to control the power provided to the heating element during the period of the gas flow.

4. The method according to claim 1, wherein the power provided to the heating element is reduced to zero for at least one period of time during the period of the gas flow.

5. The method according to claim 1, wherein the aerosol-generating device is an electrically-operated aerosol-generating device and the period of the gas flow is provided by a user puffing on the aerosol-generating device.

6. The method according to claim 1, wherein a thermal profile of the heating element increases, then decreases, and then increases again dining the period of the gas flow.

7. The method according to claim 1, wherein heating element temperature and gas flow rate are measured or calculated in real time and used to control the power provided to the heating element during the period of gas flow.

* * * * *